United States Patent
Cohen

(10) Patent No.: US 6,613,573 B1
(45) Date of Patent: Sep. 2, 2003

(54) METHOD AND APPARATUS FOR MONITORING ANTI-PLATELET AGENTS

(75) Inventor: Eli Cohen, Skokie, IL (US)

(73) Assignee: Haemoscope Corporation, Skokie, IL (US)

(*) Notice: Subject to any disclaimer, the term of this patent is extended or adjusted under 35 U.S.C. 154(b) by 363 days.

(21) Appl. No.: 09/591,371

(22) Filed: Jun. 9, 2000

Related U.S. Application Data

(63) Continuation-in-part of application No. 09/255,099, filed on Feb. 22, 1999, now Pat. No. 6,225,126.

(51) Int. Cl.$^7$ .............................................. G01N 33/86
(52) U.S. Cl. .......................... 436/69; 422/73; 600/368; 600/369; 73/64.41
(58) Field of Search ...................... 436/63, 69; 422/73; 435/13; 600/368, 369; 73/64.41

(56) References Cited

U.S. PATENT DOCUMENTS

| | | | |
|---|---|---|---|
| 5,223,227 A | 6/1993 | Zuckerman | 422/102 |
| 5,854,423 A | 12/1998 | Venegas | 73/64.41 |
| 5,972,712 A | 10/1999 | Baugh et al. | 436/69 |
| 6,225,126 B1 * | 5/2001 | Cohen et al. | 436/69 |

FOREIGN PATENT DOCUMENTS

| WO | 01/96879 | * 12/2001 | |
|---|---|---|---|

OTHER PUBLICATIONS

Dambisya et al. "Effects of the Platelet–Activating Factor Receptor Antagonist WEB 2086 on Whole Blood Coagulation and Fibrinolysis in a Thromboelastography Assay", Blood Coagulation and Fibrinolysis, vol. 6, 1995. pp. 733–737.*

Gaetano, G., et al., Effect of Platelets on Clot Structuration. A Thromebelastographic Study, *Thrombosis Research*, vol. 3, 1973, pp. 425–435.

Greilich, P., et al., "A Modified Thromboelastographic Method for Monitoring c7E3 Fab in Heparinized Patients," *Anesth Analg.*, 1997, pp. 31–38.

Khurana, S., et al., "Monitoring platelet glycoprotein llb/llla–fibrin interaction with tissue factor–activated thromboelastography," *J Lab Clin Med.*, 1997, pp. 401–411.

Timmis, G., et al., "Advances in Antiplatelet Therapy in Coronary Artery Disease: Importance of the Platelet GPIIb/IIIa Receptor," *Journal of Interventional Cardiology*, vol. 10, No. 5, 1997, pp. 327–333.

"Ultegra Rapid Platelet Function Assay (RPFA) Bedside Monitoring," Reprinted with permission from *Cath–Lab Digest*, vol. 7, No. 6, Jun. 1999, (3 pages).

Accumetrics brochure, "Ultegra System."

International Search Report for International Application No. PCT/US97/07356, filed Apr. 30, 1997.

* cited by examiner

*Primary Examiner*—Maureen M. Wallenhorst
(74) *Attorney, Agent, or Firm*—Marshall, Gerstein & Borun

(57) ABSTRACT

A blood coagulation analyzer, such as the Thrombelastograph® (TEG®) blood coagulation analyzer is utilized to measure continuously in real time, the clotting process from the initial fibrin formation, through platelet-fibrin interaction and lysis to generate blood coagulation parameters. The measured blood coagulation parameters permit confirmation of the attainment of therapeutic level of GPIIb/IIIa receptor blockade; individualized dosing assessment to evaluate attainment of adequate GPIIb/IIIa receptor blockade; individualized dosing assessment required to reach adequate GPIIb/IIIa receptor blockade; illustration of the rate of diminishment of platelet inhibition or inhibition recovery after treatment with platelet-inhibition drugs; evaluation of the interaction effect of a combination of thrombolytic or any other agents or conditions effecting hemostasis and platelet-inhibiting agents on patient hemostasis.

20 Claims, 2 Drawing Sheets

METHOD AND APPARATUS FOR MONITORING ANTI-PLATELET AGENTS

CROSS-REFERENCE TO RELATED APPLICATIONS

This application is a continuation-in-part of U.S. patent application Ser. No. 09/255,099, filed Feb. 22, 1999, entitled Method and Apparatus for Measuring Hemostasis, now U.S. Pat. No. 6,225,126, the disclosure of which is hereby expressly incorporated herein by reference.

FIELD OF THE INVENTION

The present invention relates to a method and apparatus for monitoring the efficacy of anti-platelet agents.

BACKGROUND OF INVENTION

Blood is the circulating tissue of an organism that carries oxygen and nutritive materials to the tissues and removes carbon dioxide and various metabolic products for excretion. Whole blood consists of a pale yellow or gray yellow fluid, plasma, in which are suspended red blood cells, white blood cells, and platelets.

An accurate measurement of the ability of a patient's blood to coagulate in a timely and effective fashion is crucial to certain surgical and medical procedures. Accelerated (rapid) and accurate detection of abnormal coagulations is also of particular importance in respect of appropriate treatment to be given to patients suffering from clotting disorders and to whom it may be necessary to administer anti-coagulants, antifibrinolytic agents, thrombolytic agents, anti-platelet agents, or blood components in a quantity which must clearly be determined after taking into account the abnormal components or "factors" of the patient's blood which may be contributing to the clotting disorder.

Hemostasis is a dynamic, extremely complex process involving many interacting factors, which include coagulation and fibrinolytic proteins, activators, inhibitors and cellular elements, such as platelet cytoskeleton, platelet cytoplasmic granules and platelet cell surfaces. As a result, during activation, no factor remains static or works in isolation. Thus, to be complete, it is necessary to measure continuously all phases of patient hemostasis as a net product of whole blood components in a non-isolated, or static fashion. To give an example of the consequences of the measuring of an isolated part of hemostasis, assume that a patient developed fibrinolysis, which is caused by the activation of plasminogen into plasmin, an enzyme that breaks down the clot. In this scenario, a byproduct of this process of fibrinogen degrading product (FDP), which behaves as an anticoagulant. If the patient is tested only for anticoagulation and is treated accordingly, this patient may remain at risk due to not being treated with antifibrinolytic agents.

The end result of the hemostasis process is a three-dimensional network of polymerized fibrin(ogen) fibers which together with platelet glycoprotein IIb/IIIa (GPIIb/IIIa) receptor bonding forms the final clot (FIG. 1). A unique property of this network structure is that it behaves as a rigid elastic solid, capable of resisting deforming shear stress of the circulating blood. The strength of the final clot to resist deforming shear stress is determined by the structure and density of the fibrin fiber network and by the forces exerted by the participating platelets.

Platelets have been shown to effect the mechanical strength of fibrin in at least two ways. First, by acting as node branching points, they significantly enhance fibrin structure rigidity. Secondly, by exerting a "tugging" force on fibers, by the contractability of platelet actomyosin, a muscle protein that is a part of a cytoskeleton-mediated contractibility apparatus. The force of this contractability further enhances the strength of the fibrin structure. The platelet receptor GPIIb/IIIa appears crucial in anchoring polymerizing fibers to the underlying cytoskeleton contractile apparatus in activated platelets, thereby mediating the transfer of mechanical force.

Thus the clot that develops and adheres to the damaged vascular system as a result of activated hemostasis and resists the deforming shear stress of the circulating blood is, in essence a mechanical device, formed to provide a "temporary stopper", that resists the shear force of circulating blood during vascular recovery. The kinetics, strength, and stability of the clot, that is its physical property to resist the deforming shear force of the circulating blood, determine its capacity to do the work of hemostasis, which is to stop hemorrhage without permitting inappropriate thrombosis. This is exactly what the Thrombelastograph® (TEG®) system, described below, was designed to do, which is to measure the time it takes for initial fibrin formation, the time it takes for the clot to reach its maximum strength, the actual maximum strength, and the clot's stability.

Blood coagulation analyzer instruments have been known since Professor Helmut Hartert developed such a device in Germany in the 1940's. One type of blood coagulation analyzer is described in commonly assigned U.S. Pat. No. 5,223,227, the disclosure of which is hereby expressly incorporated herein by reference. This instrument, the TEG® Coagulation Analyzer, monitors the elastic properties of blood as it is induced to clot under a low shear environment resembling sluggish venous blood flow. The patterns of changes in shear elasticity of the developing clot enable the determination of the kinetics of clot formation, as well as the strength and stability of the formed clot, in short, the mechanical properties of the developing clot. As described above, the kinetics, strength and stability of the clot provides information about the ability of the clot to perform "mechanical work", i.e., resisting the deforming shear stress of the circulating blood; in essence, the clot is the elementary machine of hemostasis, and the TEG analyzer measures the ability of the clot to perform mechanical work throughout its structural development. The TEG system measures continuously all phases of patient hemostasis as a net product of whole blood components in a non-isolated, or static fashion from the time of test initiation until initial fibrin formation, through clot rate strengthening and ultimately clot strength through fibrin platelet bonding via platelet GPIIb/IIIa receptors and clot lysis.

Platelets play a critical role in mediating ischemic complications after percutaneous transluminal coronary angioplasty (PTCA). Inhibition of the GPIIb/IIIa receptor is an extremely potent form of antiplatelet therapy that can result in dramatic reduction in the risk of death and myocardial infarction. The introduction of the murine/human chimeric antibody fragment c7E3 Fab (abciximab, ReoPro®) has resulted in the widespread availability and increasing clinical use of this therapy. Several synthetic forms of GPIIb/IIIa antagonists were recently approved, such as Aggrastat® (tirofiban) and Integrilin® (eptifibatide); with the availability of oral agents, even greater use of this form of therapy is expected.

Currently there is no rapid, reliable, quantitative, point-of-care test for monitoring therapeutic platelet blockade. Although the turbidimetric aggregation test has been used to measure the degree of platelet GPIIb/IIIa receptor blockade in small clinical studies and dose-finding studies, its routine clinical use for dosing GPIIb/IIIa receptor antagonists in individual patients has not been feasible. Aggregation is time-consuming (more than one hour), expensive to run, requires specialized personnel for its performance, and is not readily available around the clock; therefore it cannot be employed for routine patient monitoring and dose individualization. To be clinically useful, an assay of platelet inhibition must provide rapid and reliable information regarding receptor blockade at the bedside, thereby permitting dose modification to achieve the desired anti-platelet effect.

The turbidimetric aggregation test is based on the photometric principle, which monitors the change in the specimen's optical density. Initially, a minimal amount of light passes through the specimen as functional platelets are activated by the turbidimetric test; platelet aggregation occurs via platelet GPIIb/IIIa receptor and fibrin(ogen) bonding as illustrated in FIG. 1, and thus light transmission increases. When platelets are inhibited through GPIIb/IIIa receptor blockade, light transmission increases proportionally.

Another commercially available system measures fibrinogen-platelet bonding using beads coated with a fixed amount of an outside source of "normal" fibrinogen. Therefore, this system uses a non-patient source of "normal" fibrinogen and cannot detect a patient in a prothrombotic state (hypercoagulable) due to a higher patient level of fibrinogen, or detect a hemorrhagic state (hypocoagulability) due to a low patient level of fibrinogen. Additionally, this system shows only bonding without detection of the breakdown of that bonding. Therefore, in the presence of thrombolysis, the assessment of platelet GPIIb/IIIa receptor blockade by the system may not be accurate.

Fibrinogen-platelet GPIIb/IIIa bonding is the initial phase of platelet aggregation, or a primary hemostasis platelet plug, which goes on to form the final fibrin-platelet bonding. Thus it is not sufficient to measure only the initial stage of fibrinogen-platelet bonding, which may not accurately reflect final fibrin-platelet bonding via the GPIIb/IIIa receptor. While the turbidimetric and other photometric systems do detect initiation of platelet aggregation via fibrinogen-platelet GPIIb/IIIa receptor bonding, it may not accurately reflect final fibrin-platelet bonding via the GPIIb/IIIa receptor.

Significant among the limitations of systems that use beads coated with "normal" fibrinogen is that this "normal" fibrinogen may not reflect either the quantity or the functionality of a specific patient's own fibrinogen. Therefore, fibrinogen-platelet GPIIb/IIIa receptor blockade as measured by such systems is but a rough estimate of the patient's individual fibrinogen-platelet GPIIb/IIIa blockade of the initial phase of platelet aggregation.

This is a significant limitation in certain high risk patient subgroups, which may need treatment with a platelet inhibition agent, may have a higher or lower level of fibrinogen and thus would need an accurate assessment of platelet GPIIb/IIIa receptor blockade to reduce bleeding complications due to under assessment of platelet GPIIb/IIIa receptor blockade, or ischemic events due to over assessment of platelet GPIIb/IIIa receptor blockade. In addition, fibrinogen level and functionality may change during the trauma of interventional procedures. At this time it is imperative to make an accurate assessment of platelet GPIIb/IIIa receptor blockade in real time, during and following the procedure.

Thus, there is a need for a method and apparatus for measuring the efficacy of anti-platelet agents continuously and over the entire clotting process from initial clot formation through lysis.

DETAILED DESCRIPTION OF THE PREFERRED EMBODIMENTS

In accordance with the preferred embodiments of the invention, a blood coagulation analyzer, such as the Thrombelastograph® (TEG®) blood coagulation analyzer available from Haemoscope Corp., Skokie, Ill., is modified and utilized to measure continuously in real time, the clotting process from the initial fibrin formation, through platelet-fibrin GPIIb/IIIa bonding and lysis. While several specific anti-platelet agents are discussed herein in connection with the preferred embodiments of the invention, it will be appreciated the invention has application in connection with virtually any anti-platelet agents. Moreover, it will be further appreciated that the invention has application for measuring the efficacy of coagulation enhancing or platelet activating agents.

In accordance with the preferred embodiments of the invention, utilization of the blood coagulation analyzer in accordance with the inventive protocol permits: confirmation of the attainment of therapeutic level of GPIIb/IIIa receptor blockade; individualized dosing assessment to evaluate attainment of adequate GPIIb/IIIa receptor blockade; individualized dosing assessment required to reach adequate GPIIb/IIIa receptor blockade; illustration of the rate of diminishment of platelet inhibition or inhibition recovery after treatment Keith platelet-inhibition drugs; evaluation of the interaction effect of a combination of thrombolytic and platelet-inhibiting agents, on patient hemostasis.

Figure 1:
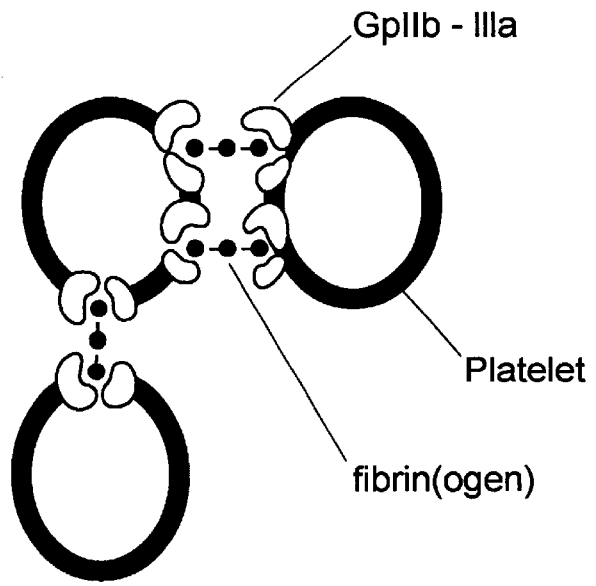
FIG. 1 is graphic illustration representing the mechanism of platelet aggregation.
Figure 2:
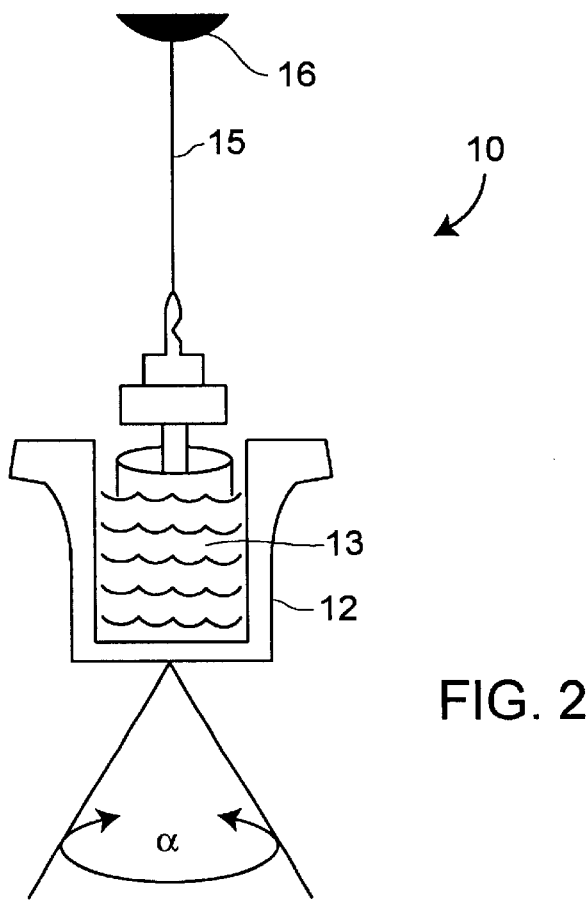
FIG. 2 is a schematic diagram of a blood coagulation analyzer in accordance with a preferred embodiment of the invention.

The present invention utilizes a blood coagulation analyzer 10, such as the Thrombelastograph® (TEG®) blood coagulation analyzer referenced above, to measure the clot's physical properties. An exemplary blood coagulation analyzer 10 is described in detail in the aforementioned U.S. patent application Ser. No. 09/255,099, and a complete discussion is not repeated here. With reference to FIG. 2, to assist in the understanding of the invention, however, a brief description of the blood coagulation analyzer 10 is provided. The blood coagulation analyzer uses a special stationary cylindrical cup 12 that holds a blood sample 13. The cup 12 is coupled to a drive mechanism that causes the cup to oscillate through an angle $\alpha$, preferably about 4°45'. Each rotation cycle lasts 10 seconds. A pin 14 is suspended in the blood sample 13 by a torsion wire 15, and the pin 14 is monitored for motion. The torque of the rotating cup 12 is transmitted to the immersed pin 14 only after fibrin-platelet bonding has linked the cup 12 and pin 14 together. The strength of these fibrin-platelet bonds affects the magnitude of the pin motion such that strong clots move the pin 14 directly in phase with the cup motion. Thus, the magnitude of the output is directly related to the strength of the formed clot. As the clot retracts or lyses, these bonds are broken and the transfer of cup motion is diminished.

The rotation movement of the pin 14 is converted by a mechanical-electrical transducer 16 to an electrical signal, which can be monitored by a computer (not shown in FIG. 2) including a processor and a control program.

The computer is operable on the electrical signal to create a hemostasis profile corresponding to the measured clotting process. Additionally, the computer may include a visual display or be coupled to a printer to provide a visual representation of the hemostasis profile. Such a configuration of the computer is well within the skills of one having ordinary skill in the art.

Figure 3:
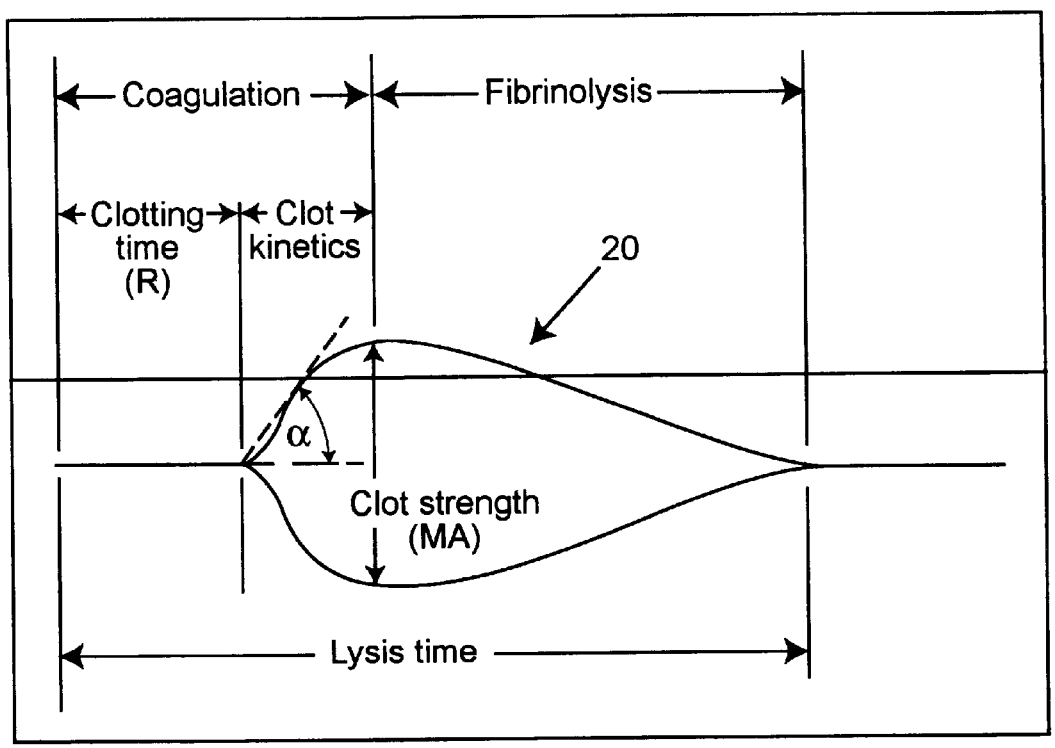
FIG. 3 is a plot illustrating a hemostasis profile generated by the blood coagulation analyzer shown in FIG. 2.

As will also be described, based upon an assessment of the hemostasis profile, the computer, through its control program, may be adapted to provide dosing recommendations. As shown in FIG. 3, the resulting hemostasis profile 20 is a measure of the time it takes for the first fibrin strand to be formed, the kinetics of clot formation, the strength of the clot (in shear elasticity units of dyn/cm$^2$) and dissolution of clot. Table I below, provides definitions for several of these measured parameters.

TABLE I

| | |
|---|---|
| R | R time is the period of time of latency from the time that the blood was placed in the TEG ® analyzer until the initial fibrin formation. |
| α | a measures the rapidity of fibrin build-up and cross-linking (clot strengthening) |
| MA | MA, or Maximum Amplitude, is a direct function of the maximum dynamic properties of fibrin and platelet bonding via GPIIb/IIIa and represents the ultimate strength of the fibrin clot. |
| LY30 | LY30 measures the rate of amplitude reduction 30 minutes after MA and represents clot retraction, or lysis. |

Clinically, these measurements provide a vehicle for monitoring anti-coagulation therapy (e.g. heparin or warfarin), thrombolytic therapy (e.g. tPA, streptokinase, urokinase), effect of antifibrinolytic (e.g. e-amino-caproic acid (Amicar®), trasylol (aprotinin), tranexamic acid (TX)), effect of anti-platelet agents (e.g. abciximab (ReoPro®), eptifibatide (Integriling®, tirofiban (Aggrastat®), blood component transfusion therapy, thrombotic risk assessment in cancer and infection, high risk surgery and other conditions which could possibly lead to excessive clotting (hypercoagulable conditions) or excessive bleeding (hypocoagulable conditions). In accordance with the invention then, the blood coagulation analyzer 10 is useful in testing the clinical efficacy of drug therapy to stop fibrinolysis, or the efficacy of thrombolytic drugs to monitor thrombolysis, efficacy of anti-platelet agents to monitor platelet inhibition, and ischemic complications.

Quantitatively, the blood coagulation analyzer 10 and associated computer plot the strength of the clot against time, where the onset of clot formation, the reaction time (R), is noted (FIG. 3). This plot also indicates the maximum clot strength (or rigidity), MA, of a blood sample. MA is an overall estimate of platelet-fibrin GPIIb/IIIa bonding, which is used, for example, to guide post-operative blood platelet or fibrinogen replacement therapy. Between platelets and fibrin alone, an abnormally low MA implies that there is an abnormality in blood platelets (i.e., a quantitative or functional defect) and/or an abnormality in fibrinogen content in the blood. However, by keeping fibrinogen level and platelet number constant, any change in MA would reflect changes in platelet function. Therefore, by testing the same blood sample two ways, one with an anti-platelet agent and one without, the difference between the two MAs reflects the effect of the anti-platelet agent on platelet function.

Platelets play a critical role in mediating ischemic complications resulting in stroke and myocardial infarction. Inhibition of platelet function by anti-platelet agents (platelet-blocker drugs) such as aspirin, the antibody fragment c7E3 Fab, abciximab (ReoPro®), or clopidogrel, (Plavix®), can result in a dramatic reduction in the risk of death, myocardial infarction, or reocclusion after percutaneous transluminal coronary angioplasty (PTCA) or intra-arterial thrombolytic therapy (IATT). Administration of excessive amounts of anti-platelet agents could lead to life-threatening bleeding. Therefore a precise estimate of platelet function inhibition in a given patient is very important for the monitoring of the drug therapy because of the narrow risk/therapeutic ratio with this class of drugs.

Using the above strategy, which keeps fibrinogen level and platelet number constant, it is possible to properly administer and monitor anti-platelet agents or modify their dosages, or to measure the contribution of fibrin to MA ($MA_{FIB}$) and by subtraction to measure the pure contribution of platelets to MA ($MA_P$) as $MA_P = MA - MA_{FIB}$.

Therefore, in accordance with the preferred embodiments of the invention, to properly monitor anti-platelet agents, the following procedure is followed:

1. The blood coagulation analyzer 10, as it is commonly used, measures platelet function (MA or $MA_P$) that is stimulated by thrombin, the most potent platelet activator. To sensitize MA or $MA_P$ to a small inhibition of platelet fuinction, platelet function should be activated by a less potent platelet activator than thrombin, such as ADP. Therefore, when running blood samples in the blood coagulation analyzer 10 in this instance, formation of thrombin is inhibited with, for example, sodium citrate, and ADP is used instead to activate the platelet function.

2. Unfortunately, thrombin is also involved in activating fibrinogen to fibrin conversion Having inhibited thrombin formation in step 1 with sodium citrate, it is necessary to use another enzyme to activate fibrinogen. Reptilase, whose sole function is to activate the fibrinogen to fibrin conversion, is a suitable enzyme. The clot is now stimulated by reptilase (fibrinogen activation) and ADP (platelet activation). The strength of the clot is measured by MA, and the contribution of platelet function to the strength of the clot is measured by $MA_P$, as described above.

3. The clot that is formed by a fibrinogen activator like reptilase and a platelet activator like ADP is typically weaker than one developed by thrombin. Therefore, the torsion wire 15 described above is selected to be sensitive to a weaker clot and to be able to measure the changes in MA and $MA_P$ due to the small effect of anti-platelet agents such as ReoPro®.

Based on the above, the following protocol may be implemented:

1. Torsion wire modification of the blood coagulation analyzer 10: by producing different strength torsion wires for various sensitivities to shear force to adequately measuring the effects of anti-platelet agents of various potencies may be measured. The sensitivity of the torsion wire is generally related to its gauge. Torsion wires having gauges to sense clot sensitivity in a range from about 150 to about 1000 dyn/cm$^2$ are suitable for adaptation to the blood coagulation analyzer described in the aforementioned U.S. patent application Ser. No. 09/255,099.

2. Reptilase-triggered agonist-activated blood sample: Batroxabin (reptilase, Pentapharm) would be used (15 μl of reconstituted reptilase reagent) would be pre-added to the cup 12 to activate fibrinogen to fibrin. In addition to the Batroxabin, ADP (20 µM final concentration) would be pre-added to the cup 12. 345 µl of citrated whole blood would be added to the prewarmed cup 12 containing Batroxabin and ADP, and maximal clot strength would be assessed. In addition, a control sample, resulting in complete inhibition of the platelet contribution the clot strength ($MA_{FIB}$), would also be performed with Batroxabin and an anti-platelet agent being added to the cup 12, providing a measure of the contribution of fibrin in the absence of the augmenting effect of platelets to clot strength.

$MA_{PB}$ is measured before the patient is treated with the anti-platelet agent and $MA_{PA}$ is measured after treatment. Platelet inhibition due to the drug effect will be computed as follows:

$$MA_{PB} = MA_B - MA_{FIB}$$

$$MA_{PA} = MA_A - MA_{FIB}$$

$$\text{Drug inhibition} = MA_{PB} - MA_{PA}$$

It will be appreciated by those having skill in the art that measuring clot strength as described above requires a torsion wire that is sensitive to the typically weaker clot formed under conditions of thrombin inhibition. However, different testing protocols may look to clots having strengths in ranges equal to or greater than typical thrombin supported clots. In such cases the torsion wire 15 will be selected to be sensitive to such stronger clots. Torsion wires of several gauges providing a range of sensitivities from about 100 dyn/cm$^2$ to 5000 dyn/cm$^2$ therefore may be utilized.

It should be further appreciated that the invention has application to measuring other parameters of clot formation. For example, the hemostasis analyzer 10 measures the blood clotting process from the time of test initiation until the initial fibrin formation, through clot rate strengthening, and clot lysis. Therefore, in accordance in the invention, it is possible to measure the effect of the presence of heparin by evaluating the R parameter, which as described above indicates the inhibition in initial fibrin formation. It is also possible to measure the efficacy of drug therapy on thrombolytic activity by observing the parameter LY30, which indicates the rate of clot lysis.

It is well-documented that there is considerable person-to-person variability in the number of GPIIb/IIIa receptors per platelet and its ligand binding function. Furthermore, variable inhibition of GPIIb/IIIa function, in part due to the differences in platelet count, may occur after administration of a fixed, weight-adjusted dose of a platelet blocker. Higher risk patient subgroups, such as diabetic patients undergoing PTCA, may require greater doses of platelet inhibition than is currently, being attained after weight-adjusted platelet blocker therapy, which at this time is not individualized to assure the attainment of adequate GPIIb/IIIa receptor blockade. The potential for hemorrhagic or ischemic events suggests the need for individualized assessment and projecting of needed dosing to assure the attainment of a therapeutic level of receptor blockade, in real time. The apparatus and method in accordance with the preferred embodiments of the invention provides this capability.

The invention has been described in terms of several preferred embodiments. One of skill in the art will appreciate that the invention may be otherwise embodied without departing from its fair scope, which is set forth in the subjoined claims.

We claim:

1. An apparatus for measuring the efficacy of an anti-platelet therapy comprising:
   a blood coagulation analyzer operable to measure a first blood sample in the absence of the anti-platelet therapy and a second blood sample in the presence of the anti-platelet therapy to respectively generate a first blood coagulation parameter and a second blood coagulation parameter, wherein the first blood coagulation parameter and the second blood coagulation parameter are related to blood clot strength; and
   a processor operatively coupled to the blood coagulation analyzer, the processor having an associated control program for directing the operation of the processor for determining an efficacy of the anti-platelet therapy based upon the first blood coagulation parameter and the second blood coagulation parameter, wherein at least one of the first blood coagulation parameter and the second blood coagulation parameter is based upon a characteristic of an as sampled portion of the respective blood sample and a characteristic of a portion of the respective blood sample treated in vitro to inhibit thrombin activation and to preserve fibrinogen and platelet activation.

2. The apparatus of claim 1, wherein each of the first blood coagulation parameter and the second blood coagulation parameter is based upon a characteristic of an as sampled portion of the respective blood sample and a characteristic of a portion of the respective blood sample treated in vitro to inhibit thrombin activation and to preserve fibrinogen and platelet activation.

3. The apparatus of claim 1, wherein the blood coagulation analyzer has a clot strength sensitivity in the range of about 100 dyn/cm$^2$ to about 1000 dyn/cm$^2$.

4. The apparatus of claim 1, wherein the blood coagulation analyzer includes a first testing station and a second testing station, the first and second testing stations operable substantially simultaneously on the first blood sample and the second blood sample, respectively.

5. The apparatus of claim 4, wherein the first testing station has a first clot strength sensitivity and the second testing station has a second clot strength sensitivity.

6. The apparatus of claim 1, wherein the processor and control program are further operable to generate data for providing a visual representation of the first and second blood coagulation parameters.

7. The apparatus of claim 1, wherein the processor and control program are further operable to generate a dosing recommendation associated with the anti-platelet therapy.

8. The apparatus of claim 1, wherein at least one of the first and second blood coagulation parameters relate to a blood coagulation therapy comprising one of: an anti-coagulation therapy utilizing the administration of heparin or warfarin; a thrombolytic therapy utilizing the administration of tPA, streptokinase or urokinase; an antifibrinolytic therapy utilizing ε-amino-caproic acid or trasylo, tranexamic acid; an anti-platelet therapy; and a blood component transfusion therapy.

9. The apparatus of claim 1, wherein at least one of the first and second parameters relate to a thrombotic risk assessment including a hypercoagulable condition assessment and an excessive bleeding risk including hypocoagulable assessment.

10. A method of measuring the efficacy of an anti-platelet therapy comprising the steps of:
   providing a blood coagulation analyzer, the blood coagulation analyzer capable of measuring a clot strength;

determining a first blood coagulation parameter of a first blood sample obtained in the absence of the anti-platelet therapy using the blood coagulation analyzer;

determining a second blood coagulation parameter of a second blood sample obtained in the presence of the anti-platelet therapy using the blood coagulation analyzer;

wherein at least one of the first blood coagulation parameter and the second blood coagulation parameter is based upon a characteristic of an as sampled portion of the respective blood sample and a characteristic of a portion of the respective blood sample treated in vitro to inhibit thrombin activation and to preserve fibrinogen and platelet activation; and determining an efficacy of the anti-platelet therapy based on the first and second blood coagulation parameters.

11. The method of claim 10, wherein the blood coagulation analyzer is operable to measure a clot strength in the range of about 100 dyn/cm$^2$ to about 1000 dyn/cm$^2$.

12. The method of claim 10, wherein the blood coagulation analyzer provides for the substantially simultaneous testing of the first and second blood samples.

13. The method of claim 10, performed in conjunction with the administration of at least one of the following blood coagulation therapies: anti-coagulation therapy utilizing the administration of heparin or warfarin; a thromolytic therapy utilizing the administration of tPA, streptokinase or urokinase; an antifibrinolytic therapy utilizing e-amino-caproic acid, trasylol or tranexamic acid; an anti-platelet therapy and a blood component transfusion therapy.

14. The method of claim 10, wherein the method is performed in connection with assessment of thrombotic risk.

15. The method of claim 10, wherein the method is performed in connection with one of an assessment of a hypercoagulable condition and a hypocoagulable condition.

16. The method of claim 10, further comprising the step of determining a dosing of an anti-platelet agent.

17. The method of claim 10, wherein the blood coagulation analyzer comprises processing capability, and wherein the step of determining an efficacy is performed by the blood coagulation analyzer.

18. The method of claim 10, wherein the first and second blood coagulation parameters are based upon one of: a latency period to clot formation, a rate of clot formation, a maximum clot strength and rate of clot lysis.

19. The method of claim 10, wherein the first and second blood coagulation parameters correspond to an estimate of fibrin-platelet interaction.

20. The method of claim 10, wherein the first blood coagulation parameter is represented by a first maximum amplitude measurement and the second coagulation parameter is represented by a second maximum amplitude measurement, and wherein the step of determining an efficacy comprises comparing the first maximum amplitude with the second maximum amplitude.

* * * * *

UNITED STATES PATENT AND TRADEMARK OFFICE
CERTIFICATE OF CORRECTION

PATENT NO. : 6,613,573 B1
DATED : September 2, 2003
INVENTOR(S) : Eli Cohen

It is certified that error appears in the above-identified patent and that said Letters Patent is hereby corrected as shown below:

Column 2,
Line 57, please delete the phrase "ReoPro®has" and insert -- ReoPro®) has --.

Column 4,
Line 38, please delete the phrase "treatment Keith" and insert -- treatment with --.

Column 5,
Line 16, please delete the phrase "Table I below," and insert -- Table I, below, --.
Line 23, please delete the phrase "a measures" and insert -- α measures --.
Line 38, please delete the phrase "(Integriling®, tirofiban" and insert -- (Integrilin®), tirofiban --.

Column 6,
Line 26, please delete the phrase "platelet fuinction" and insert -- platelet function --.
Line 34, please delete the phrase "conversion Having" and insert -- conversion. Having --.

Column 8,
Line 56, please delete the phrase "∈-amino" and insert -- ε-amino --.

Signed and Sealed this

Sixth Day of January, 2004

JAMES E. ROGAN
*Director of the United States Patent and Trademark Office*